United States Patent [19]

Price

[11] Patent Number: 5,616,477
[45] Date of Patent: Apr. 1, 1997

[54] FUSION PROTEINS COMPRISING GM-CSF AND ANTIGENS AND THEIR EXPRESSION IN YEAST

[75] Inventor: Virginia L. Price, Seattle, Wash.

[73] Assignee: Immunex Corporation, Seattle, Wash.

[21] Appl. No.: 641,704

[22] Filed: May 2, 1996

Related U.S. Application Data

[63] Continuation of Ser. No. 271,875, Jul. 7, 1994, abandoned.

[51] Int. Cl.$^6$ .............................. C12N 1/19; C12N 15/27; C12N 15/62
[52] U.S. Cl. .................... 435/69.5; 435/69.7; 435/252.3; 435/320.1; 536/23.4
[58] Field of Search ................................. 435/69.5, 69.7, 435/252.3, 320.1; 536/23.4

[56] References Cited

FOREIGN PATENT DOCUMENTS

0604727A1 7/1994 European Pat. Off. .

OTHER PUBLICATIONS

B. M. Curtis et al., *P.N.A.S.* 88:5809–5813, Jul. 1991.

V. Price, *Gene* 55:287–293, 1987.

Tao and Levy, *Nature*, 362:755–758 (1993).

Dranoff et al., *Proc. Natl. Acad. Sci. USA* 90:3539 (1993).

*Primary Examiner*—John Ulm
*Attorney, Agent, or Firm*—Patricia Anne Perkins; Charlene Launer

[57] ABSTRACT

Novel fusion proteins that enhance the immune response of an antigen are efficiently expressed and secreted by yeast host cells. The fusion proteins are recombinantly made by fusing the 3'-end of mature GM-CSF DNA sequence to the 5'-end of an antigen DNA sequence with or without a linker sequence. Methods of expression in yeast cells are provided.

23 Claims, No Drawings

FUSION PROTEINS COMPRISING GM-CSF AND ANTIGENS AND THEIR EXPRESSION IN YEAST

CROSS REFERENCE TO RELATED APPLICATION

This application is a continuation of application Ser. No. 08/271,875, filed Jul. 7, 1994, now abandoned.

BACKGROUND OF THE INVENTION

The present invention relates generally to the construction of fusion proteins that enhance the immune response of an antigen and are efficiently expressed and secreted by yeast host cells. More specifically, the invention relates to yeast recombinant expression systems for producing fusion proteins comprising a granulocyte-macrophage colony-stimulating factor (GM-CSF) domain fused to a selected antigen domain.

Technologies for the efficient production of large quantities of antigenic proteins for use as immunogens have been sought for many years. Genes encoding protein antigens and fragments of antigens comprising particular epitopes have been expressed in prokaryotic and eukaryotic cell expression systems with varying degrees of success. To elicit an antibody response in animals, administration of adjuvants, repeated administration of the expressed protein, or both often were needed.

Certain materials have been shown to have adjuvant activity, including for example alum, fragments of bacterial membranes, liposomes, coupling a protein of interest to a larger immunogenic protein, RIBI, and TiterMax®. Of all of them, alum is the only adjuvant licensed by the Food and Drug Administration for use in humans. Some investigators have attempted to chemically couple adjuvants to antigens. Such coupling involves harsh treatment and often results in destruction of a portion of the antigen and reduced antigenicity.

Some cytokines, e.g., interleukin-4 (IL-4) and GM-CSF, attract and activate antigen-presenting cells for more efficient presentation of antigens to T cells. These cytokines have been co-administered with antigen to increase antigenic activity. Other studies have shown that the host response to tumor challenge can be increased by inoculation of tumor cells genetically engineered to express particular cytokines, including γ-INF, TNF-α, IL-2, IL-4, IL-6, IL-7, or GM-CSF.

Further, Tao and Levy (*Nature*, 362: 755–758 (1993)) created chimeric tumor idiotype/GM-CSF fusion proteins as vaccines for B-cell lymphoma. They created their fusion proteins by constructing plasmids with a coding sequence of a heavy-chain variable region from a mouse B-cell tumor inserted upstream of a human IgG1 heavy-chain constant region gene and a restriction cite generated next to the last codon of the CH3 exon into which genetic fragments encoding either murine or human GM-CSF were inserted. These heavy chain vectors were then cotransfected with a light chain chimeric constructs into a malignant plasma cell tumor. The proteins made by the transfected cells were tetrameric proteins that were dimeric with respect to GM-CSF.

Research continues toward enhancing the immune response of an antigen. Proteins that have the bioactivity of both cytokines and antigens will provide the advantages of using chemically defined antigenic entities and eliminating the need to separately administer or co-administer cytokines and antigens or inoculate patients with genetically modified living tumor cells.

SUMMARY OF THE INVENTION

Novel fusion proteins comprising either mature murine or human GM-CSF fused to a selected antigen are efficiently expressed in yeast at very high levels, with virtually all the material made being secreted from the yeast. The fusion proteins are created using standard molecular biology techniques to fuse the 3'-end of mature GM-CSF DNA sequence to the 5'-end of an antigen DNA sequence. The GM-CSF DNA sequence is fused to the antigen DNA sequence with or without a linker peptide sequence. DNA encoding the GM-CSF/antigen fusion protein is operably linked to suitable transcriptional or translational regulatory elements. Preferably, the regulatory elements include an ADH2 promoter and a secretion signal is either a yeast α-factor leader or a type I interleukin-1 receptor (IL-1R) signal sequence lacking its native signal peptidase recognition site. Yeast cells transformed with the resulting expression vector are cultivated to express and secrete large quantities of the desired fusion protein, that are recovered from the culture supernatant. These fusion proteins have the biological activity of both GM-CSF and the antigen.

The invention also provides for methods of producing a GM-CSF/antigen fusion protein that has the biological activity of both GM-CSF and the selected antigen. One such method includes ligating the 3'-end of a DNA sequence encoding mature GM-CSF to the 5'-end of a DNA sequence encoding a selected antigen; linking the ligated DNA sequences to regulatory elements that are responsible for expression of DNA into a single biologically active protein; inserting the ligated DNA sequence into a yeast host cell, culturing the yeast host cell under conditions promoting expression; and recovering the desired fusion protein from the culture. The regulatory elements preferably include an ADH2 promoter and a secretion signal that is either a yeast α-factor leader or a type I interleukin-1 receptor (IL-1R) signal sequence lacking its native signal peptidase recognition site.

A second method includes culturing a yeast cell transformed with an expression vector comprising a promoter, a sequence encoding GM-CSF fused in frame to the 5'-end of a DNA sequence encoding an antigen, and a stop codon under conditions that promote expression of said fusion protein; and recovering the desired fusion protein from said culture. Preferably, the promoter is an ADH2 promoter. Further, the expression vector preferably includes a secretion signal is either a yeast α-factor leader or a type I interleukin-1 receptor (IL-1R) signal sequence lacking its native signal peptidase recognition site.

DETAILED DESCRIPTION OF THE INVENTION

As used herein, the term "GM-CSF" refers to proteins having amino acid sequences that are substantially similar to the native human granulocyte-macrophage colony-stimulating factor amino acid sequences (e.g., ATCC 53157) and that are biologically active in that they are capable of binding to GM-CSF receptors, transducing a biological signal initiated by binding GM-CSF receptors, or cross-reacting with antibodies raised against GM-CSF. Such sequences are disclosed, for example, by Anderson et al. in *Proc. Nat'l. Acad. Sci. USA* 82: 6250 (1985). The term "GM-CSF" also includes analogs of GM-CSF molecules that exhibit at least some biological activity in common with native human GM-CSF. Exemplary analogs of GM-CSF are disclosed in EP Publ. No. 212914 (U.S. Ser. No. 06/763,130), which describes GM-CSF analogs having KEX2 protease cleavage sites inactivated so as to increase expression of GM-CSF in yeast hosts, and in WO Publ. No. 89/03881 (U.S. Pat. No. 5,032,676), which describes GM-CSF analogs having various glycosylation sites eliminated.

The term "antigen" refers to a tumor antigen or foreign protein that induces the formation of antibodies that interact specifically with it. Each antigen may contain more than one site (antigenic determinant) capable of binding to a particular antibody. Thus, an antigen can cause the production of a number of antibodies with different specificities. A "foreign protein" refers to a protein other than one encoded by or derived from the human genome; e.g., a microbial or viral protein or parasite protein.

"Biologically active" as used herein means that a particular molecule shares sufficient amino acid sequence similarity with native forms so as to be capable of binding to native receptors, transmitting a stimulus to a cell, or cross-reacting with antibodies raised against the particular molecule.

As used herein, the term "fusion protein" refers to an antigen fused to the C-terminal portion of GM-CSF. Specifically, the fusion proteins of the present invention have a formula selected from the group consisting of $$R_1\text{-}L\text{-}R_2 \text{ or } R_1\text{-}R_2$$

wherein $R_1$ is GM-CSF; $R_2$ is an antigen; and L is a peptide linker sequence. The antigen is linked to GM-CSF in such a manner as to produce a single protein that retains the biological activity of the native antigen and mature GM-CSF. Unless otherwise specified, the term "GM-CSF/antigen" refers to fusion protein with a peptide linker sequence added.

"Recombinant expression vector" refers to replicable DNA constructs that contain a synthetic or cDNA-derived DNA sequence encoding one of the above-described fusion proteins, operably linked to suitable transcriptional or translational regulatory elements. Examples of genetic elements having a regulatory role in gene expression include transcriptional promoters, operators or enhancers, a sequence encoding suitable mRNA ribosomal binding sites, and appropriate transcription and translation initiation and termination sequences. The ability to replicate in a host, usually conferred by an origin of replication, and a selection gene to facilitate recognition of transformants may additionally be incorporated. The regulatory elements employed in the expression vectors that are conventionally used to express recombinant proteins in *S. cerevisiae* may be used. Regulatory elements for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

DNA regions are operably linked when they are functionally related to each other. A DNA sequence encoding a fusion protein is operably linked to one or more of the above-described regulatory elements when the fusion protein DNA sequence is transcribed, or the resulting mRNA is translated, under the control of the regulatory element(s). For example, DNA for a signal peptide (secretory leader) is operably linked to DNA for a polypeptide if it is expressed as a precursor that participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

"Transformed host cells" are cells that have been transformed or transfected with foreign DNA using recombinant DNA techniques. In the context of the present invention, the foreign DNA includes a sequence encoding the inventive fusion protein. Host cells may be transformed for purposes of cloning or amplifying the foreign DNA, or may be transformed with an expression vector for production of the fusion protein under the control of appropriate promoters. Examples of appropriate cloning and expression vectors for use with yeast hosts are described by Pouwels et al. in *Cloning Vectors: A Laboratory Manual*, Elsevier, N.Y. (1985). Cell-free translation systems also could be employed to produce fusion protein using RNAs derived from the DNA constructs of the present invention.

A "DNA sequence" refers to a DNA polymer, in the form of a separate fragment or as a component of a larger DNA construct, that has been derived from DNA isolated at least once in substantially pure form (i.e., free of contaminating endogenous materials) and in a quantity or concentration enabling identification, manipulation, and recovery of its component nucleotide sequences by standard biochemical methods such as those outlined by Sambrook et al. in *Molecular Cloning: A Laboratory Manual*, 2nd ed., Cold Spring Harbor Laboratory, Cold Spring Harbor, N.Y. (1989). Such sequences are preferably provided in the form of an open reading frame uninterrupted by internal nontranslated sequences, or introns, that are typically present in eukaryotic genes. Sequences of non-translated DNA may be present 5' or 3' from an open reading frame, where the same do not interfere with manipulation or expression of the coding regions.

"Nucleotide sequence" refers to a heteropolymer of deoxyribonucleotides. DNA sequences encoding the proteins provided by this invention may be assembled from cDNA fragments and short oligonucleotide linkers, or from a series of oligonucleotides, to provide a synthetic gene that is capable of being expressed in a recombinant transcriptional unit.

The term "heterologous protein" as used herein indicates that the protein to be expressed is not naturally expressed in the yeast host cell.

Fusion Proteins and Analogs

The present invention provides fusion proteins comprising a murine or human GM-CSF domain and a selected antigen. The fusion proteins also may include a linker peptide between the GM-CSF and the antigen.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini. Other derivatives of the fusion protein within the scope of this invention include covalent or aggregative conjugates of the fusion protein with other proteins or polypeptides.

Peptides also may be added to facilitate purification or identification of GM-CSF/antigen fusion proteins (e.g., poly-His). The amino acid sequence of the fusion protein also can be linked to the peptide disclosed by Hopp et al. in

*Bio/Technology* 6: 1204, (1988). The latter sequence is highly antigenic and provides an epitope reversibly bound by a specific monoclonal antibody, enabling rapid assay and facile purification of expressed recombinant protein.

Derivatives and analogs may be obtained by mutations of the fusion protein. A derivative or analog is a polypeptide in which the GM-CSF or antigen domains are substantially homologous to the native GM-CSF (e.g., ATCC 53157) and the native antigen of choice but have an amino acid sequence difference attributable to a deletion, insertion or substitution.

Bioequivalent analogs of GM-CSF or antigen domains to be incorporated into the fusion proteins may be constructed by making various substitutions of amino acid residues or sequences, or by deleting terminal or internal residues or sequences not needed for biological activity. For example, Cys residues can be deleted or replaced with other amino acids to prevent formation of incorrect intramolecular disulfide bridges upon renaturation. Other approaches to mutagenesis involve modification of dibasic amino acid residues to enhance expression in yeast systems in which KEX2 protease activity is present. Generally, substitutions are made conservatively by substituting an amino acid having physiochemical characteristics resembling those of the native residue.

Mutations in nucleotide sequences constructed for expression of analogs must, of course, preserve the reading frame phase of the coding sequences and preferably will not create complementary regions that could hybridize to produce secondary mRNA structures such as loops or hairpins that would adversely affect translation of the GM-CSF/antigen mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for the desired activity.

Not all mutations in nucleotide sequences that encode fusion proteins comprising GM-CSF and the antigen of choice will be expressed in the final product. For example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. In addition, the polymerase chain reaction (PCR) can be used to generate mutant DNA sequences.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. in *Gene* 42: 133 (1986); Bauer et al. in *Gene* 37: 73 (1985); Craik in *BioTechniques* p. 12–19 (January 1985); Smith et al. in *Genetic Engineering: Principles and Methods*, Plenum Press (1981); and U.S. Pat. Nos. 4,518,584 and 4,737,462, and are incorporated by reference herein.

Source of Recombinant Fusion Proteins Comprising GM-CSF and an Antigen

A DNA sequence encoding a fusion protein is constructed using recombinant DNA techniques to assemble separate DNA sequences encoding GM-CSF and the antigen into an appropriate expression vector. The 3' end of a DNA sequence encoding mature GM-CSF is ligated, with or without a peptide linker, to the 5' end of the DNA sequence encoding a biologically active antigen of choice, so that the reading frames of the sequences are in phase to permit mRNA translation of the two DNA sequences into a single biologically active fusion protein. The resulting protein is a GM-CSF/antigen fusion protein.

In preferred aspects of the present invention, a peptide linker sequence is incorporated into the fusion protein construct by well-known standard molecular biology techniques (e.g., PCR). The linker sequence is used to separate GM-CSF and the antigen domains by a distance sufficient to ensure that each domain properly folds into its secondary and tertiary structures. Suitable peptide linker sequences (1) will adopt a flexible extended conformation, (2) will not exhibit a propensity for developing an ordered secondary structure that could interact with the functional GM-CSF and antigen domains, and (3) will have minimal hydrophobic or charged character that could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Thus, amino acid sequences useful as linkers of GM-CSF and antigen include the $Gly_4SerGly_5Ser$ linker (SEQ ID NO 1) used in U.S. Pat. No. 5,108,910 or a series of four (Ala Gly Ser) residues (SEQ ID NO 2). Still other amino acid sequences that may be used as linkers are disclosed in Maratea et al., *Gene* 40: 39–46 (1985); Murphy et al., *Proc. Nat'l. Acad. Sci. USA* 83: 8258–62 (1986); U.S. Pat. No. 4,935,233; and U.S. Pat. No. 4,751,180.

The length of the peptide linker sequence may vary without significantly affecting the biological activity of the fusion protein. In one preferred embodiment of the present invention, a peptide linker sequence length of about 12 amino acids is used to provide a suitable separation of functional protein domains, although longer linker sequences also may be used. The linker sequence may be from 1 to 50 amino acids in length. In the most preferred aspects of the present invention, the linker sequence is from about 1–20 amino acids in length. In the specific embodiments disclosed herein, the linker sequence is from about 5 to about 15 amino acids, and is advantageously from about 10 to about 15 amino acids. Peptide linker sequences are unnecessary where the proteins being fused have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the GM-CSF cDNA fragment, while these regulatory elements or stop codons that would prevent read-through to the antigen DNA fragment, are not present on the GM-CSF fragment. Conversely, regulatory elements are not present on the antigen DNA fragment while stop codons required to end translation and transcription termination signals are present only 3' to the antigen DNA fragment.

Expression of Recombinant Fusion Proteins Comprising GM-CSF and an Antigen

The present invention provides for recombinant expression vectors that include synthetic or cDNA-derived DNA fragments encoding fusion proteins comprising GM-CSF and an antigen of choice or bioequivalent analogs operably linked to suitable transcriptional or translational regulatory elements. The regulatory elements include a transcriptional promoter, an optional operator sequence to control transcription, a sequence encoding suitable mRNA ribosomal binding sites, and sequences that control the termination of transcription and translation, as described in detail below. The ability to replicate in a host, usually conferred by an origin of replication, and a selection gene to facilitate recognition of transformants may additionally be incorporated.

The fusion protein vectors are transformed or transfected into host cells. Transformed host cells ordinarily express the desired fusion protein, but host cells transformed for purposes of cloning or amplifying DNA do not need to express the protein. Expressed fusion protein will generally be secreted into the culture supernatant. The present invention provides for expression of the inventive fusion proteins in yeast under the control of appropriate regulatory elements.

Our recombinant fusion proteins are expressed in yeast hosts, preferably from the Saccharomyces species, such as *S. cerevisiae*. Yeast of other genera such as Pichia or Kluyveromyces also may be employed. Those skilled in the art will readily see that other expression systems, such as mammalian and insect expression systems with appropriate regulatory elements, also can be used to express the desired fusion protein. Secretion of the desired protein from the yeast cells is advantageous since the desired protein is recovered from the culture supernatant rather than from the complex mixture of proteins that results when yeast cells are disrupted to release intracellular proteins. Secretion also reduces the deleterious (e.g., toxic) effect that intracellular accumulation of a given foreign protein may have on the host cell.

The yeast *S. cerevisiae* is often used for the expression and secretion of heterologous proteins. Efficient, high-level secretion of a cerevisiae protein from yeast requires not only efficient transcription and translation of the mRNA, but at the posttranslational level, efficient processing of the leader sequence that directs secretion and routing through the secretory pathway. Efficient processing of a signal (pre) or additional pro sequences used to direct secretion first requires enzymatic cleavage at the signal peptidase site and, if present, additional cleavage at the 3' end of the pro sequence (the KEX2 site for the alpha-factor leader). If the signal sequence fails to be cleaved off in the endoplasmic reticulum, the protein does not continue through the secretory pathway. Similarly, if the additional processing site(s) at the 3' end of a pro region are not cleaved, secretion is either greatly inhibited, or if it does occur, the desired protein has additional amino acids at the N-terminus. See, e.g., Brake et. al., *Proc. Nat'l. Acad. Sci.*, 81: 4642–4646 (1984). The particular amino acid sequences that are present 3' to these cleavage sites have an effect on the ability of the sites to be processed. Some heterologous amino acid sequences fused 3' to a secretion signal cause inefficient cleavage, thus poor secretion while others allow efficient cleavage, thus good secretion. Human and murine GM-CSF are examples of heterologous proteins that can be secreted from yeast at very high levels, with virtually all the material made being secreted from the yeast.

We have found that the presence of the N-terminal sequences of GM-CSF fused 3' of either the signal peptidase site present on the type I IL-1R signal sequence (described below) or the KEX2 site present on the α-factor pro region allow efficient processing of these signals. With any different heterologous protein placed immediately 3' to the processing signals, it is unknown whether there would be efficient processing, thus secretion. If a heterologous cDNA were fused 3' to the GM-CSF gene, the junction between the signal or pro processing sites and GM-CSF would be maintained and one would expect to achieve efficient processing and secretion of the fusion molecule. Any additional benefits of the GM-CSF protein and its ability to "route" through the secretory system would be maintained, too. The fusion to GM-CSF thus eliminates one of the key variables in secretion of heterologous proteins in yeast. Such a fusion system for expression in yeast is ideally suited to the fusion of peptides (5–50 amino acids) or relatively small proteins of about a molecular mass of 20,000 daltons or less to GM-CSF. For the expression of antigens larger than 30,000 daltons, those of ordinary skill in the art can design an analogous system for expression in mammalian or insect cells or other yeasts.

*S. cerevisiae* strain YIMX9 is particularly useful as a host cell of the expression of GM-CSF/antigen fusion proteins. The YIMX9 strain was generated and isolated as follows. The procedures are generally as described in Rose et al., *Methods in Yeast Genetics, A Laboratory Course Manual*, Cold Spring Harbor Press, Cold Spring Harbor, N.Y., pages 13–15 (1990). *S. cerevisiae* strain XV617-1-3B [a, his6, leu2-1, trpl-1, ura3, ste5] was obtained University of Washington, Department of Genetics Yeast Strain Bank, Seattle, Wash. A fresh overnight culture of XV617-1-3B transformed with a recombinant expression vector was grown in YEPG (1% yeast extract, 2% peptone, 2% glucose) to a cell density of about $1–2 \times 10^8$ cells/ml. The vector encoded a reporter protein that is not well secreted from this strain. The culture was diluted to $5 \times 10^7$ cells/ml in $KH_2PO_4$, pH 7.0, 10 mls total volume. 0.45 ml of the mutagen ethylmethane sulfonate (EMS, available from Sigma Chemical Co., St. Louis, Mo.) was added, and the culture was incubated at 30° C. for 30 minutes. Cells were then plated at a density of 500–1000 cells/plate on YNB ⁻trp medium (0.67% yeast nitrogen base, 2% glucose, amino acids minus tryptophan at approximately 20 μg/ml).

Colonies were screened for secretion of the reporter protein using an antibody immunoreactive with the reporter protein. Positive colonies were detected by binding of the antibody to secreted product on nitrocellulose filters. A mutant isolated from this screening process was designated YIMX1. Strain YIMX1 was crossed to strain X2181-1B [a, trpl-1, gall, adel, his2], obtained from the Yeast Genetic Stock Center, University of California, Berkeley, Calif., to create the diploid strain designated YIMX2. This diploid is heterozygous at the mutant locus (an unidentified locus that allows improved secretion of the reporter protein). The mutation of interest was shown to be recessive in that strain YIMX2 did not exhibit the property of better secretion of the reporter protein. For this reason, UV mutagenesis was performed on YIMX2 to induce homozygosis at the mutant locus (a crossing-over event that would result in information from one chromosome replacing that on the homologous chromosome).

YIMX2 was transformed with the reporter-encoding expression vector employed in the first mutagenesis procedure. The UV source was a Stratalinker® UV Crosslinker (Stratagene Cloning Systems, LaJolla, Calif.), that emits about 0.67 mjoules per second. YNB ⁻trp plates spread with $0.5–1 \times 10^3$ colonies per plate were irradiated for 12–15 seconds. Colonies were screened as above for increased secretion of the reporter protein. A strain demonstrating increased secretion of the reporter protein was isolated and designated YIMX9. A sample of the isolated mutant strain *S. cerevisiae* YIMX9 was deposited under the terms of the Budapest Treaty with the American Type Culture Collection in Rockville, Md., and assigned accession number ATCC 74224.

Another particularly useful host cell is the *S. cerevisiae* strain designated XV2181 (a/α, trp1; V. Price et al., *Gene*, 55: 287–293 (1987)). XV2181 was formed by mating the above-described strains XV617-1-3B and X2181-1B.

Appropriate cloning and expression vectors for use with yeast are described herein and by Pouwels et al. in *Cloning Vectors: A Laboratory Manual*, Elsevier, N.Y. (1985). Expression vectors generally comprise one or more phenotypic selectable markers (e.g., a gene encoding a protein that confers antibiotic resistance or that supplies an autotrophic requirement) and an origin of replication recognized by the intended host cell to ensure amplification within the host. Yeast vectors commonly contain an origin of replication from the 2 μm yeast plasmid or an autonomously replicating sequence (ARS), a promoter, DNA encoding the fusion protein, sequences for polyadenylation and transcription termination and a selectable marker. Some yeast vectors will include an origin of replication and selectable marker permitting transformation of both yeast and *E. coli*, e.g., the ampicillin resistance gene of *E. coli* and *S. cerevisiae* TRP1 gene, that provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255: 2073 (1980)) or glycolytic enzymes (Hess et al., *J. Adv. Enzyme Reg.* 7: 149 (1968); and Holland et al., *Biochem.* 17: 4900 (1978)), such as the ADH2 promoter (Russell et al. in *J. Biol. Chem.* 258: 2674 (1982) and Beier et al. in *Nature* 300: 724 (1982)), enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Yeast secreted proteins generally are initially expressed as precursors bearing an N-terminal signal or leader peptide. Signal peptides generally contain a positively charged N-terminus followed by a hydrophobic core, followed by a recognition site for an enzyme known as signal peptidase. This enzyme cleaves the signal peptide from the protein during translocation. The protein is transported from the endoplasmic reticulum to the Golgi apparatus, and then follows one of a number of routes in the secretory pathway, depending on the nature of the protein. The protein may be secreted into the culture medium or may be retained on the cell surface, for example. Certain receptors that comprise extracellular, transmembrane, and cytoplasmic domains are examples of proteins that may be retained on the cell membrane, with only the extracellular domain located outside the cell.

The leader sequences of certain secreted proteins comprise peptides that are located C-terminal to the signal peptide and are processed from the mature protein of interest subsequent to cleavage of the signal peptide. Such leaders often are referred to as prepro peptides, wherein the pre region is the signal sequence and the pro region designates the remainder of the leader. One example is the yeast α-factor leader, that contains a signal peptide (including a C-terminal signal peptidase recognition site AlaLeuAla) followed by a pro region containing a basic amino acid pair LysArg that constitutes a KEX2 protease processing site, immediately followed by a peptide GluAlaGluAla at the C-terminus of the pro region. Processing of this leader involves removal of the signal peptide by signal peptidase, followed by cleavage between the Lys and Arg residues by KEX2 protease. The GluAlaGluAla residues are subsequently removed by a peptidase that is the product of the STE13 gene (Julius et al., *Cell* 32: 839 (1983)). The yeast α-factor leader is described in U.S. Pat. No. 4,546,082.

The yeast expression vector advantageously comprises DNA encoding a suitable leader or signal peptide fused to the 5' end of the DNA encoding the fusion protein. The leader peptide thus is fused to the N-terminus of the fusion protein when initially expressed, and promotes secretion of the expressed fusion protein from the cell. The leader peptide is cleaved by specific intracellular protease(s) during secretion, so that the fusion protein recovered from the culture medium does not have the leader peptide attached thereto.

Any signal or leader peptide recognized by *S. cerevisiae* cells may be employed. Examples are the leader or signal peptide of such proteins as the *S. cerevisiae* α-factor MFα1 (described in U.S. Pat. No. 4,546,082), *S. cerevisiae* invertase, encoded by the SUC2 gene (Smith et al., *Science* 229: 1219, 1985; Chang et al., *Mol. Cell. Biol.* 6: 1812, 1986), *S. cerevisiae* acid phosphatase, encoded by PH05 (Smith et al., 1985, supra; Hinnen et al. in Korhola and Vaisanen, Eds., *Gene Expression in Yeast, Foundation for Biotechnological and Industrial Fermentation Research*, Vol. 1, Kauppakirjapaino Oy, Helsinki, 1983, pp. 157–163), *S. carlsbergensis* α-galactosidase (the MEL1 gene product) (Hofmann and Schultz, *Gene* 101: 105, 1991), *K. lactis* killer toxin (ORF2) (Stark and Boyd, *EMBO J.* 5: 1995, 1986; Baldari et al., *EMBO J.* 6: 229, 1987), *S. cerevisiae* killer toxin (Tokunaga et al., *Nuc. Acids res.* 16: 7499, 1988), and the *S. cerevisiae* BGL2 gene product (Achstetter et al., *Gene* 110: 25, 1992). The pre or prepro region of a given leader (discussed above) may be employed.

Preferably, a signal peptide derived from a type I interleukin-1 receptor (IL-1R) signal sequence lacking its native signal peptidase recognition site is used. This signal peptide has the formula sig[Z]$_n$AlaXala, wherein sig represents a truncated type I interleukin-1 receptor signal sequence lacking the amino acids at positions y through −1 of the native signal sequence, wherein y is −3 or −4. The sig moiety is derived from the signal sequence of a type I interleukin-1 receptor. Such signal sequences include the human and murine type I IL-1 receptor signal sequences described in U.S. Pat. No. 5,081,228 (hereby incorporated by reference) or homologous signal peptides derived from other mammalian species.

Z represents an optional spacer peptide comprising from 1–5 amino acids, preferably 1–3 amino acids; and n is 0 or 1. Z contains neither the native signal peptidase recognition site of the intefieukin-1 receptor signal sequence, nor a tripepride of the formula AlaXAla. One example of Z is a peptide encoded by a linker useful for constructing a recombinant vector, e.g., a linker containing a desired restriction site. The AlaXAla tripeptide replaces the native signal peptidase recognition site. X is an amino acid selected from the group consisting of Leu, Phe, and Gln, preferably Leu. For expression of a desired fusion protein, DNA encoding the fusion protein is fused to the 3' end of the DNA segment encoding this signal peptide.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The yeast α-factor leader, that directs secretion of heterologous proteins, can be inserted between the promoter and the structural gene to be expressed. See, e.g., Kurjan et al., *Cell* 30: 933 (1982); and Bitter et al., *Proc. Natl. Acad. Sci. USA* 81: 5330 (1984). The leader sequence may be modified to contain, near its 3' end, one or more useful restriction sites to facilitate fusion of the leader sequence to foreign genes.

A particularly preferred eukaryotic yeast vector for expression of GM-CSF/antigen DNA is pIXY456. pIXY456 is a derivative of the pαADH2 yeast expression plasmid described by V. Price et al. in *Gene*, 55: 287–293 (1987); the phage f1 origin of replication in pIXY456 does not exist in pαADH2.

Suitable yeast transformation protocols are known to those of skill in the art; an exemplary technique is described by Hinnen et al. in *Proc. Natl. Acad. Sci. USA* 75: 1929 (1978), selecting for Trp$^+$ transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by centrifugation are filtered and held at 4° C. prior to further purification.

Purified fusion proteins or analogs are prepared by culturing suitable host/vector systems to express the recombinant translation products of the DNAs of the present invention, that are then purified from culture media or cell extracts. For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a GM-CSF receptor or lectin or antibody molecule bound to a suitable support.

Fermentation of yeast that express fusion proteins as a secreted protein greatly simplifies purification. Secreted recombinant protein resulting from a large-scale fermentation can be purified by methods analogous to those disclosed by Urdal et al. in *J. Chromatog.* 296: 171 (1984). This reference describes two sequential, reverse-phase HPLC steps for purification of recombinant murine GM-CSF on a preparative HPLC column.

Fusion protein synthesized in recombinant culture is characterized by the presence of unwanted and unknown proteins (contaminants) in amounts and of a character that depend upon the purification steps taken to recover the fusion protein from the culture. These components ordinarily will be of yeast origin and preferably are present in innocuous contaminant quantities, on the order of less than about 5 percent by scanning densitometry or chromatography. Further, recombinant cell culture enables the production of the fusion protein free of proteins that may be normally associated with GM-CSF or the antigen as they are found in nature in their respective species of origin, e.g., in cells, cell exudates or body fluids.

Fusion protein compositions are prepared for administration by mixing fusion protein having the desired degree of purity with physiologically acceptable carriers. Such carriers will be nontoxic to recipients at the dosages and concentrations employed. Ordinarily, the preparation of such compositions entails combining the fusion protein with buffers, antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients.

The following examples are offered by way of illustration, and not by way of limitation.

EXAMPLE 1

Construction of muGM-CSF/Malaria Antigen Yeast Expression Vectors

Yeast expression plasmid pIXY456 was digested with the restriction enzymes Asp718 and SpeI and the large vector fragment was purified using standard molecular biology techniques. DNA encoding the murine GM-CSF gene (muGM-CSF; *PNAS* 82: 6250 (1985)) was amplified using the polymerase chain reaction (PCR). PCR primer sequences used were SEQ ID NO 3 for the 5' primer and SEQ ID NO 4 for the 3' primer. The 5' primer included an Asp718 restriction site to fuse the muGM-CSF in-frame to the Asp718 site in the α-factor leader, regenerating the 3' end of the leader. The 3' primer included a portion of the Gly$_4$SerGly$_5$Ser linker (amino acid sequence Gly-Gly-Gly-Gly-Ser) and a BamH1 site.

A DNA fragment encoding the gene for the Pfs25 malarial antigen (*Nature*, 333: 74–76 (1988) and *Bio/technology*, 12: 494–499 (1994)) also was generated using the polymerase chain reaction in such a way as to add the 3' end of the Gly$_4$SerGly$_5$Ser linker from the BamH1 site (nucleic acids 5 through 28 of SEQ ID NO 5) at the 5' end of antigen and to add a Spe1 restriction site after the termination codon for the gene. Thus the malarial antigen PCR primer sequences used were SEQ ID NO 5 for the 5' primer and SEQ ID NO 6 for the 3' primer.

The PCR product encoding muGM-CSF+linker was purified and digested with the enzymes Asp718 and BamH1. Similarly, the PCR product encoding the Pfs25 antigen was purified and digested with the enzymes BamH1 and Spe1. These two DNA fragments were ligated into the Asp718-Spe1 cut vector described above. This created a fusion DNA construct encoding muGM-CSF-linker-Pfs25 antigen. The linker has the sequence of SEQ ID NO 1.

*S. cerevisiae* strain XV2181 cells were transformed by conventional techniques with muGM-CSF-linker-Pfs25 antigen DNA construct. The transformed cells were cultured in 1 liter shake flasks in 1% yeast extract, 2% peptone, and 1% glucose supplemented with 80 µg/ml adenine and 80 µg/ml uracil. Derepression of the ADH2 promoter occurred when glucose is exhausted from the medium. After cultivation for about 24–28 hours to permit expression and secretion of the soluble fusion protein into the supernatant, the cells were pelleted by centrifugation and the supernatant (culture medium) was filtered.

Supernatants containing the soluble fusion protein were purified. First, they were first concentrated using a commercially available protein concentration filter (an Amicon or Millipore Pellicon ultrafiltration unit). Following the concentration step, the concentrate was purified by using nickel agarose to select for the poly-his tail. Alternatively, reverse-phase HPLC methods analogous to those disclosed by Urdal et al. in *J. Chromatog.* 296: 171 (1984) can be used.

The filtered supernatants or purified fusion proteins were analyzed for muGM-CSF biological activity and Pfs25 antigen presence. To test for muGM-CSF activity, proliferation of the muGM-CSF factor dependent cell line FCDP-2-1D was used to measure the GM-CSF-biological activity of the supernatants or purified fusion proteins. The results for the purified muGM-CSF-linker-Pfs25 antigen fusion proteins were similar to those for the muGM-CSF clone disclosed in *PNAS* 82: 6250 (1985). The filtered supernatants and purified fusion proteins also tested positive in murine bone marrow colony assays. To test for Pfs25 antigen presence within the fusion proteins, antigen-antibody reactions with Pfs25 antigen-specific antibodies were used with positive results. After as few as one innoculation, murine animals inoculated with the muGM-CSF-linker-Pfs25 antigen fusion proteins should have significantly higher antibody tilers to Pfs25 than those inoculated with Pfs25 antigen alone.

EXAMPLE 2

Construction of Other muGM-CSF/Antigen Yeast Expression Vectors

The vector from Example 1 containing the muGM-CSF gene fused in-frame to a $Gly_4SerGly_5Ser$ linker and the Pfs25 antigen was then used to generate other muGM-CSF fusion expression plasmids. The fusion DNA construct encoding muGM-CSF-linker-Pfs25 antigen from Example 1 was digested with BamH1 and Spe1 and the large vector fragment containing the DNA encoding muGM-CSF and a portion of the $Gly_4SerGly_5Ser$ linker was purified. The DNA sequences encoding other antigens (e.g., the MSP1 malarial antigen disclosed by Kaslow et al. in *Molecular and Biochemical Parasitology* 63: 283–289 (1994) and *Haemophilus influenzae* outer membrane lipoprotein disclosed by Deich et al in *J. Bacteriology* 170(2): 489–498 (1988)) were amplified using the polymerase chain reaction in such a way as to create the BamH1 site at their 5' terminus and the remainder of the $Gly_4SerGly_5Ser$ linker sequence. This allowed ligation of the antigen sequence in-frame to the muGM-CSF-linker sequence at the BamH1 site. The 3' PCR primer included a Spe1 site at the 3' end after the termination codon.

*S. cerevisiae* strain XV2181 cells were transformed by conventional techniques with either the muGM-CSF-linker-MSP1 antigen DNA construct or the muGM-CSF-linker-*H. influenzae* OMP DNA construct. The transformed cells were cultured as described above in Example 1. Supernatants containing the soluble muGM-CSF-linker-MSP 1 fusion proteins were purified as described in Example 1. Supernatant containing the soluble muGM-CSF-linker-*H. influenzae* OMP fusion proteins were purified using reverse-phase HPLC methods analogous to those disclosed by Urdal et al. in *J. Chromatog.* 296: 171 (1984).

The filtered supernatants or purified fusion proteins were analyzed for muGM-CSF biological activity as described in Example 1 with positive results. To test for *H. influenzae* OMP-antigen presence within the fusion proteins, antigen-antibody reactions using *H. influenzae* OMP-antigen-specific antibodies were used with positive results. To test for MSP1-antigen presence within the fusion proteins, antigen-antibody reactions with MSP1-antigen-specific antibodies were used with positive results.

Additionally, after one inoculation, mice inoculated with the GM-CSF-linker-MSP1 fusion protein demonstrated a significant increase in antibody titer to MSP1 over those inoculated with MSP1 alone. The increased antibody titer demonstrated the enhanced antigenic response elicited by GM-fusions. After as few as one innoculation, murine animals inoculated with the muGM-CSF-linker-*H. influenzae* OMP antigen fusion proteins should have significantly higher antibody titers to *H. influenzae* OMP than those inoculated with *H. influenzae* OMP antigen alone.

EXAMPLE 3

Construction of a huGM-CSF/*H. influenzae* OMP Antigen Yeast Expression Vectors

Using methods similar to those described in Example 1, vectors also are created using DNA encoding human GM-CSF (huGM-CSF; e.g., ATCC 53157) in place of muGM-CSF to create a huGM-CSF-linker-Pfs25 antigen fusion DNA construct. PCR primer sequences used are SEQ ID NO 7 for the 5' primer and SEQ ID NO 8 for the 3' primer. The 5' primer included an Asp718 restriction site to fuse the muGM-CSF in-frame to the Asp718 site in the α-factor leader, regenerating the 3' end of the leader. The 3' primer included a portion of the $Gly_4SerGly_5Ser$ linker to the BamH1 site (amino acid sequence Gly-Gly-Gly-Gly-Ser).

A DNA sequence encoding *Haemophilus influenzae* outer membrane lipoprotein disclosed by Deich et al in *J. Bacteriology* 170(2): 489–498 (1988) was generated using the polymerase chain reaction in such a way as to create the BamH1 site at the 5' terminus and the remainder of the $Gly_4SerGly_5Ser$ linker sequence. The PCR product encoding muGM-CSF+linker was purified and digested with the enzymes Asp718 and BamH1. Similarly, the PCR product encoding the *H. influenzae* OMP antigen was purified and digested with the enzymes BamH1 and Spe1. These two DNA fragments were ligated into the Asp718-Spe1 cut vector described above. This created a fusion DNA construct encoding huGM-CSF-linker-*H. influenzae* OMP antigen.

Conventional techniques and the huGM-CSF-linker-*H. influenzae* OMP DNA construct were then used to transform *S. cerevisiae* cells. The transformed cells were cultured as described above in Example 1. Supernatant containing the soluble huGM-CSF-linker-*H. influenzae* OMP fusion proteins were purified using reverse-phase HPLC methods analogous to those disclosed by Urdal et al. in *J. Chromatog.* 296: 171 (1984).

The purified fusion proteins are analyzed for huGM-CSF biological activity and *H. influenzae* OMP antigen presence. To test for huGM-CSF biological activity, proliferation of the huGM-CSF factor dependent cell line TF-1 is used to measure the GM-CSF-biological activity of the secreted fusion proteins. The results for the purified huGM-CSF-linker-*H. influenzae* OMP antigen fusion proteins were similar to those for huGM-CSF (ATCC 53157). The filtered supernatants and purified fusion proteins also tested positive in human bone marrow colony assays. To test for *H. influenzae* OMP antigen presence within the fusion proteins, antigen-antibody reactions using *H. influenzae* OMP-antigen-specifie antibodies were used with positive results. After as few as one inoculation, animals or humans inoculated with the huGM-CSF-linker-*H. influenzae* OMP antigen fusion protein should have significantly higher antibody tilers to *H. influenzae* OMP than those inoculated with *H. influenzae* OMP antigen alone.

EXAMPLE 4

Construction of huGM-CSF/Malaria Antigen Yeast Expression Vectors

Similar to the process described in Example 2, the huGM-CSF-linker-*H. influenzae* OMP antigen fusion DNA construct of Example 3 can be used to generate other huGM-CSF fusion expression plasmids. For example, the fusion DNA construct encoding huGM-CSF-linker-*H. influenzae* OMP antigen from Example 3 is digested with BamH1 and Spe1 and the large vector fragment containing the DNA encoding muGM-CSF and a portion of the $Gly_4SerGly_5Ser$ linker was purified.

A DNA fragment encoding the gene for the Pfs25 malarial antigen can be generated using the polymerase chain reaction in such a way as to create the BamH1 site at the 5' terminus and the remainder of the $Gly_4SerGly_5Ser$ linker sequence. This allows ligation of the antigen sequence in-frame to the huGM-CSF-linker sequence at the BamH1 Site.

*S. cerevisiae* strain XV2181 cells or YIMX9 cells are transformed by conventional techniques with the huGM-CSF-linker-Pfs25 antigen. The transformed cells are cultured as described above in Example 1. Supernatants containing the soluble huGM-CSF-linker-Pfs25 antigen fusion proteins are purified using the same methods used for purification of the muGM-CSF-linker-Pfs25 antigen fusion proteins in Example 1.

The purified fusion proteins are analyzed for huGM-CSF biological activity as described in Example 3. To test for Pfs25 antigen presence within the secreted fusion proteins, antigen-antibody reactions described in Example 1 are used. After as few as one innoculation, animals or humans inoculated with the huGM-CSF-linker-Pfs25 antigen fusion proteins should have significantly higher antibody titers to Pfs25 than those inoculated with Pfs25 antigen alone.

EXAMPLE 5

Construction of Alternative Linkered muGM-CSF/Malaria Antigen Yeast Expression Vectors A yeast expression vector similar to the ones described in Example 1 above can be made with a (Ala Gly Ser)$_4$ linker instead of the $Gly_4SerGly_5Ser$ linker. As in Example 1, yeast expression plasmid pIXY456 is digested with the restriction enzymes Asp718 and Spe1 and the large vector fragment is purified using standard molecular biology techniques. DNA encoding the murine GM-CSF gene (muGM-CSF; *PNAS* 82: 6250 (1985)) is amplified using the polymerase chain reaction (PCR). Instead of SEQ ID NOs 3 and 4 in Example 1, PCR primer SEQ ID NO 3 for the 5' primer and SEQ ID NO 9 for the 3' primer are used. The 5' primer includes an Asp718 restriction site to fuse the muGM-CSF in-frame to the Asp718 site in the α-factor leader, regenerating the 3' end of the leader.

A DNA fragment encoding the gene for the Pfs25 malarial antigen also is generated using the polymerase chain reaction in such a way as to add the 3' end of the (Ala Gly Ser)$_4$ linker from the BamH1 site (nucleic acids 5 through 10 of SEQ ID NO 10) at the 5' end of antigen and to add a Spe1 restriction site after the termination codon for the gene. Thus the malarial antigen PCR primer sequences used are SEQ ID NO 10 for the 5' primer and SEQ ID NO 6 for the 3' primer.

The PCR product encoding muGM-CSF+linker is purified and digested with the enzymes Asp718 and BamH1. Similarly, the PCR product encoding the Pfs25 antigen is purified and digested with the enzymes BamH1 and Spe1. These two DNA fragments are ligated into the Asp718-Spe1 cut vector described above. This creates a fusion DNA construct encoding muGM-CSF-linker-Pfs25 antigen. The linker has the sequence of SEQ ID NO 2.

*S. cerevisiae* strain XV2181 cells or YIMX9 cells are transformed by conventional techniques with muGM-CSF-linker-Pfs25 antigen DNA construct. The transformed cells are cultured as described above in Example 1. Supernatants containing the soluble fusion protein are purified as described in Example 1. The purified fusion proteins are analyzed for muGM-CSF biological activity as described in Example 1. To test for Pfs25 antigen presence within the fusion proteins, antigen-antibody reactions with Pfs25 antigen-specific antibodies are used. After as few as one innoculation, murine animals inoculated with the muGM-CSF-linker-Pfs25 antigen fusion proteins should have significantly higher antibody titers to Pfs25 than those inoculated with Pfs25 antigen alone.

Similar to the process described in Example 2, the muGM-CSF-linker-Pfs25 antigen fusion DNA construct of this example can be used to generate other muGM-CSF fusion expression plasmids.

EXAMPLE 6

Construction of Alternative Linkered huGM-CSF/Malaria Antigen Yeast Expression Vectors Yeast expression vectors similar to the ones described in Example 3 above can be made with an (Ala Gly Ser)$_4$ linker instead of the $Gly_4SerGly_5Ser$ linker. As in Example 3, yeast expression plasmid pIXY456 is digested with the restriction enzymes Asp718 and Spe1 and the large vector fragment is purified using standard molecular biology techniques. DNA encoding the huGM-CSF gene is amplified using the polymerase chain reaction (PCR). Instead of SEQ ID NOs 7 and 8 in Example 3, PCR primer SEQ ID NO 7 for the 5' primer and SEQ ID NO 11 for the 3' primer are used. The 5' primer includes an Asp718 restriction site to fuse the huGM-CSF in-frame to the Asp718 site in the α-factor leader, regenerating the 3' end of the leader. The 3' primer includes a portion of the (Ala Gly Ser)$_4$ linker and a BamH1 site.

A DNA fragment encoding the gene for the Pfs25 malarial antigen also is generated using the polymerase chain reaction in such a way as to add the 3' end of the (Ala Gly Ser)$_4$ linker from the BamH1 site (nucleic acids 5 through 10 of SEQ ID NO 10) at the 5' end of antigen and to add a Spe1 restriction site after the termination codon for the gene. Thus the malarial antigen PCR primer sequences used are SEQ ID NO 10 for the 5' primer and SEQ ID NO 6 for the 3' primer.

The PCR product encoding huGM-CSF+linker is purified and digested with the enzymes Asp718 and BamH1. Similarly, the PCR product encoding the Pfs25 antigen is purified and digested with the enzymes BamH1 and Spe1. These two DNA fragments are ligated into the Asp718-Spe1 cut vector described above. This creates a fusion DNA construct encoding huGM-CSF-linker-Pfs25 antigen. The linker has the sequence of SEQ ID NO 2.

*S. cerevisiae* strain XV2181 cells or YIMX9 cells are transformed by conventional techniques with huGM-CSF-linker-Pfs25 antigen DNA construct. The transformed cells are cultured as described above in Example 1. Supernatants containing the soluble fusion protein are purified as described in Example 1.

To test purified fusion proteins for huGM-CSF biological activity, proliferation of the huGM-CSF factor dependent cell line TF-1 is used to measure the huGM-CSF-biological activity of the supernatants and fusion proteins. Alternatively, huGM-CSF biological activity can be used using human bone marrow colony assays. To test for the presence of Pfs25 antigen within the fusion proteins, antigen-antibody reactions described in Example 1 are used. After as few as one innoculation, animals or humans inoculated with the muGM-CSF-linker-Pfs25 antigen fusion proteins should have significantly higher antibody titers to Pfs25 than those inoculated with Pfs25 antigen alone.

Similar to the process described in Examples 2 and 4, the huGM-CSF-linker-Pfs25 antigen fusion DNA construct of this example can be used to generate other huGM-CSF fusion expression plasmids.

EXAMPLE 7

Construction of Linkerless GM-CSF-Antigen Yeast Expression Vector

Yeast expression vectors similar to the ones described in Example 1 through 6 above also can be made without a linker. As in Examples 1 through 6, yeast expression plasmid pIXY456 is digested with the restriction enzymes Asp718 and Spe1 and the large vector fragment is purified using standard molecular biology techniques. DNA encoding the human or murine GM-CSF gene is amplified using the polymerase chain reaction (PCR). The 5' primer includes an Asp718 restriction site to fuse the GM-CSF in-frame to the Asp718 site in the α-factor leader, regenerating the 3' end of the leader.

A DNA fragment encoding the antigen of choice is generated using the polymerase chain reaction in such a way as to fuse it to GM-CSF at the 5' end of the antigen and to add a Spe1 restriction site after the termination codon for the gene. Depending on sequence, a restriction site can be created near the junction of the two cDNAs. The GM-CSF and antigen DNA fragments are ligated into the Asp718-Spe1 cut vector described above. This creates a fusion DNA construct encoding a linkerless human or murine GM-CSF-antigen DNA fusion construct that may be used to transform yeast host cells.

Alternatively, oligonucleotide-directed site-specific mutagenesis procedures can be employed to provide a linkerless GM-CSF/antigen fusion by deleting the linker sequences from any one of the constructs of Examples 1 through 6. Exemplary methods of making such a deletion are disclosed by Walder et al. in *Gene* 42: 133 (1986); Bauer et al. in *Gene* 37: 73 (1985); *Craik in BioTechniques* p. 12–19 (January 1985); Smith et al. in *Genetic Engineering: Principles and Methods*, Plenum Press (1981 ); and U.S. Pat. Nos. 4,518,584 and 4,737,462, and are incorporated herein by reference. The construct formed may be used to transform yeast host cells.

The transformed cells are cultured as described in any of the examples provided above. After cultivation for about 24–28 hours to permit expression and secretion of the soluble fusion protein into the supernatant, the cells are pelleted by centrifugation and the supernatant (culture medium) is filtered. Supernatants containing the soluble fusion protein are purified and tested for biological activity as described in the examples above. After as few as one innoculation, murine animals or humans inoculated with the linkerless murine or human GM-antigen fusion proteins should have significantly higher antibody titers to the antigen than those inoculated with the antigen alone.

What is claimed is:

1. A DNA encoding a fusion protein that has the biological activity of both GM-CSF and an antigen selected from the group consisting of a tumor antigen, a microbial protein, a viral protein, and a parasite protein, comprising a DNA encoding mature GM-CSF fused to a DNA encoding the antigen, wherein the 3'-end of said GM-CSF DNA is fused to the 5'-end of said antigen DNA.

2. The DNA of claim 1, wherein said GM-CSF DNA is fused to said antigen DNA via a DNA encoding a linker peptide.

3. The DNA of claim 2, wherein said linker peptide DNA encodes a peptide selected from the group consisting of (Ala Gly Ser)$_4$ and Gly$_4$SerGly$_5$Ser.

4. A recombinant expression vector for expression of a fusion protein in a yeast cell, comprising a DNA encoding a fusion protein that has the biological activity of both GM-CSF and an antigen selected from the group consisting of a tumor antigen, a microbial protein, a viral protein, and a parasite protein, comprising a DNA encoding mature GM-CSF fused to a DNA encoding the antigen, wherein the 3'-end of said GM-CSF DNA is fused to the 5'-end of said antigen DNA, operably linked to a promoter and a secretion signal.

5. The recombinant expression vector of claim 4, wherein said promoter is ADH2 and said secretion signal is selected from the group consisting of a yeast α-factor leader and a type I interleukin-1 receptor (IL-1R) signal sequence lacking its native signal peptidase recognition site.

6. A yeast host cell transformed or transfected with an expression vector according to claim 4.

7. The host cell of claim 6, wherein said host cell is *Saccharomyces cerevisiae*.

8. A process for preparing a fusion protein comprising GM-CSF and an antigen, comprising culturing a yeast host cell according to claim 6 under conditions promoting expression and recovering a polypeptide from the culture that has the biological activity of both GM-CSF and said antigen.

9. A recombinant expression vector for expression of a fusion protein in a yeast cell, comprising a DNA encoding a fusion protein that has the biological activity of both GM-CSF and an antigen selected from the group consisting of a tumor antigen, a microbial protein, a viral protein, and a parasite protein, comprising a DNA encoding mature GM-CSF fused to a DNA encoding the antigen, wherein the 3'-end of said GM-CSF DNA is fused to the 5'-end of said antigen DNA, operably linked to a promoter and a secretion signal, wherein said GM-CSF DNA is fused to said antigen DNA via a DNA encoding a linker peptide.

10. The recombinant expression vector of claim 9, wherein said promoter is ADH2 and said secretion signal is selected from the group consisting of a yeast α-factor leader and a type I interleukin-1 receptor (IL-1R) signal sequence lacking its native signal peptidase recognition site.

11. A yeast host cell transformed or transfected with an expression vector according to claim 6.

12. The host cell of claim 11, wherein said host cell is *Saccharomyces cerevisiae*.

13. A process for preparing a fusion protein comprising GM-CSF and an antigen, comprising culturing a yeast host cell according to claim 11 under conditions promoting expression and recovering a polypeptide from the culture that has the biological activity of both GM-CSF and said antigen.

14. A method of making a GM-CSF/antigen fusion protein that has the biological activity of both GM-CSF and said antigen, wherein said antigen is selected from the group consisting of a tumor antigen, a microbial proteins a viral protein, and a parasite protein, comprising the steps of:

ligating the 3'-end of a DNA encoding mature GM-CSF to the 5'-end of a DNA encoding an antigen;

linking said ligated DNA to regulatory elements that are responsible for expression of DNA into a single biologically active protein;

inserting said ligated DNA into a yeast host cell;

culturing said yeast host cell under conditions promoting expression; and recovering said fusion protein from said culture.

15. The method of claim 14, wherein GM-CSF DNA is ligated to said antigen DNA via a DNA encoding a linker peptide.

16. The method of claim 15, wherein said linker peptide is selected from the group consisting of (Ala Gly Ser)$_4$ and Gly$_4$SerGly$_5$Ser.

17. The method of claim 14, wherein said regulatory elements are selected from the group consisting of a transcriptional promoter, an optional sequence to control transcription, and a stop codon.

18. The method of claim 17, wherein said promoter is ADH2.

19. The method of claim 17, wherein said regulatory elements further comprise a DNA encoding a secretion signal selected from the group consisting of a yeast α-factor leader and a type I interleukin-1 receptor (IL-1R) signal sequence lacking its native signal peptidase recognition site.

20. The method of claim 14, wherein said yeast host cell is *Saccharomyces cerevisiae*.

21. A method of making a GM-CSF/antigen fusion protein that has the biological activity of both GM-CSF and said antigen, wherein said antigen is selected from the group consisting of a tumor antigen, a microbial protein, a viral protein, and a parasite protein, comprising the steps of:

culturing said yeast cell transformed with an expression vector comprising a promoter, a DNA encoding mature GM-CSF fused to the 5'-end of a DNA encoding an antigen, and a stop codon under conditions that promote expression of said fusion protein; and recovering said fusion protein from said culture.

22. The method of claim 21, wherein said promoter is ADH2.

23. The method of claim 21, wherein said expression vector further comprises a DNA encoding a secretion signal selected from the group consisting of a yeast α-factor leader and a type I interleukin-I receptor (IL-1R) signal sequence lacking its native signal peptidase recognition site.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Gly Gly Gly Gly Ser Gly Gly Gly Gly Gly Ser
1               5                   10
```

( 2 ) INFORMATION FOR SEQ ID NO:2:

( i ) SEQUENCE CHARACTERISTICS:
( A ) LENGTH: 12 amino acids
( B ) TYPE: amino acid
( C ) STRANDEDNESS: single
( D ) TOPOLOGY: linear (i i) MOLECULE TYPE: peptide (i i i) HYPOTHETICAL: NO (i v) ANTI-SENSE: NO (x i) SEQUENCE DESCRIPTION: SEQ ID NO:2:

```
Ala  Gly  Ser  Ala  Gly  Ser  Ala  Gly  Ser  Ala  Gly  Ser
 1                  5                        10
```

(2) INFORMATION FOR SEQ ID NO:3:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:3:

```
ATATGGTACC  TTTGGATAAA  AGAGAGGCTG  AAGCCTCTTT  GGATAAAAGA  GCACCCACCC    60

GCTCACCCAT  C                                                            71
```

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:4:

```
CCCCGGATCC  ACCGCCACCT  TTTTGGACTG  GTTTTTTGCA                            40
```

(2) INFORMATION FOR SEQ ID NO:5:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:5:

```
AATTGGATCC  GGGGGTGGCG  GCGGCTCAGC  TAAGGTCACT  GTCGACACCG  TC            52
```

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:6:

AATTACTAGT TCAGTGGTGG TGGTGGTGGT GTGGATCGGT AC    42

(2) INFORMATION FOR SEQ ID NO:7:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:7:

ATATGGTACC TTTGGATAAA AGAGAGGCTG AAGCCTCTTT GGATAAAAGA GCTCCAGCTA    60

GATCTCCATC T    71

(2) INFORMATION FOR SEQ ID NO:8:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:8:

CCCCGGATCC ACCGCCACCC TCCTGGACTG GCTCCCAGCA    40

(2) INFORMATION FOR SEQ ID NO:9:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:9:

AATTGGATCC AGCAGAGCCG GCAGAGCCAG CAGAACCAGC TTTTGGACT GGTTTTTGC    60

A    61

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:10:

AATTGGATCC GCTAAGGTCA CTGTCGACAC CGTC  34

(2) INFORMATION FOR SEQ ID NO:11:

(i) SEQUENCE CHARACTERISTICS:
  (A) LENGTH: 60 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:11:

AATTGGATCC AGCAGAGCCG GCAGAGCCAG CAGAACCAGC CTCCTGGACT GGCTCCAGC  60